US00PP29917P2

(12) United States Plant Patent
Hansen

(10) Patent No.: US PP29,917 P2
(45) Date of Patent: Nov. 27, 2018

(54) **X *MANGAVE* PLANT NAMED 'SPOTTY DOTTY'**

(50) Latin Name: ***x Mangave* times *Agave***
Varietal Denomination: Spotty Dotty

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/732,274

(22) Filed: Oct. 17, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique X *Mangave* plant named 'Spotty Dotty' characterized by long, broad, straight, foliage, that develop small reddish-purple spots densely covering the upper and lower surfaces. Leaves have small and medium sized semi-flexible marginal spines and semi-flexible apical spine. Growth rate is rapid to moderate. The new plant is suitable for the garden or as a potted plant in the garden or home.

1 Drawing Sheet

Botanical classification: hybrid; x *Mangave* times *Agave*.
Variety denomination: 'Spotty Dotty'.

BACKGROUND OF THE INVENTION

The present invention relates to the new and distinct X *Mangave* hybrid plant, X *Mangave* 'Spotty Dotty' hybridized by the inventor at a wholesale perennial nursery in Zeeland, Mich., USA as cross between a proprietary unreleased hybrid known only by the breeder code X *Mangave* H10-2 (not patented) as the female or seed parent times a selection of *Agave bovicornuta* (not patented) as the male or pollen parent. The cross was performed on Apr. 17, 2012 and seeds were harvested and sown on Aug. 1, 2012. After trials at the same nursery the plant was assigned the breeder code XMANG-12-18-7. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of X *Mangave* 'Spotty Dotty' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

X *Mangave* 'Spotty Dotty' differs from its parents as well as all other *Manfreda, Agave* and X *Mangave* known to the applicant. The most similar known cultivars are X *Mangave* 'Moonglow' U.S. Plant Pat. No. 29,195, X *Mangave* 'Inkblot' U.S. Plant Pat. No. 29,431 and X *Mangave* 'Pineapple Express' U.S. Plant Pat. No. 28,613. In comparison, the female parent the leaves that are wider and has a lighter shade of green and the habit is flatter and less arching.

Compared with the male parent the new plant has longer, narrower, more fleshy and more flexible foliage, with smaller and more flexible marginal spines, and heavy coverage of small reddish-purple coloration. 'Moonglow' differs from the new plant in having shorter, narrower, less arching foliage with more glaucous, silvery blue-green color and larger greyed-purple spotting. Compared with 'Inkblot' the new plant has broader leaves with smaller dots of reddish purple. Compared to 'Pineapple Express' U.S. Plant Pat. No. 28,613 the new plant has longer and broader leaves that have smaller and more consistently-sized reddish-purple coloration.

The new plant, 'Spotty Dotty', is unique from all of the above cultivars and all *Agave*, X *Mangave* and *Manfreda* known to the inventor by the following combined traits:

1. Long, broad, straight, slightly-wavy, foliage;
2. Leaves develop small dots of reddish-purple spots densely covering throughout upper and lower surfaces;
3. Both medium and small-sized, semi-flexible teeth on leaf margins and semi-flexible apical spine;
4. Moderate to rapid growth rate.

BRIEF DESCRIPTION OF THE DRAWING

The photographs of x *Mangave* 'Spotty Dotty'; demonstrates the overall appearance of the new plant including the unique traits as a three-year-old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
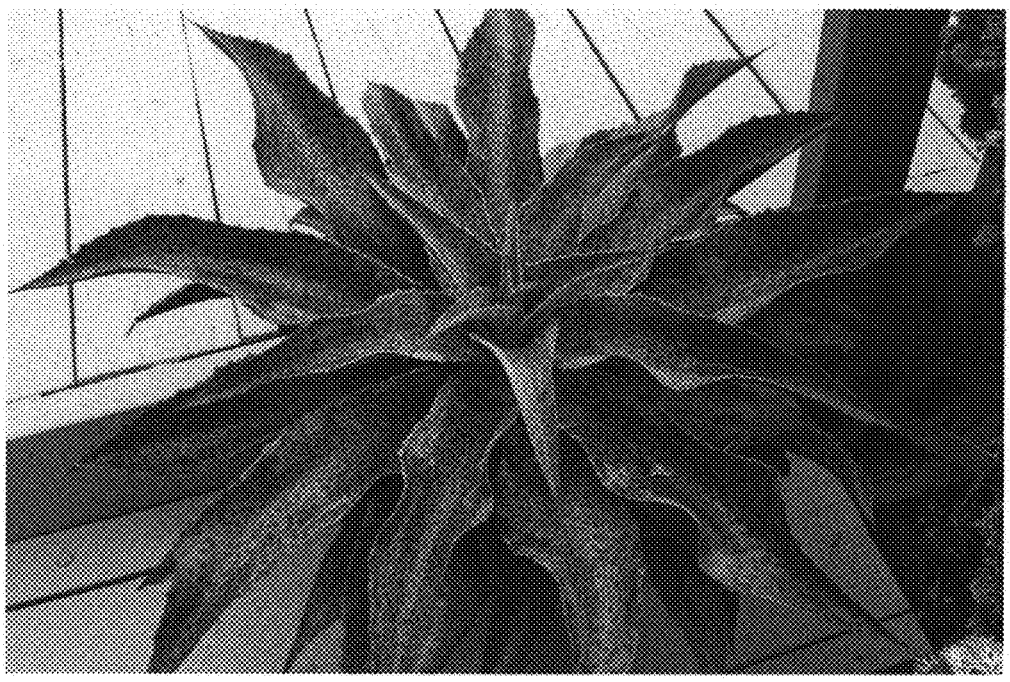
FIG. 1 shows the new plant having been grown in a container.
Figure 2:
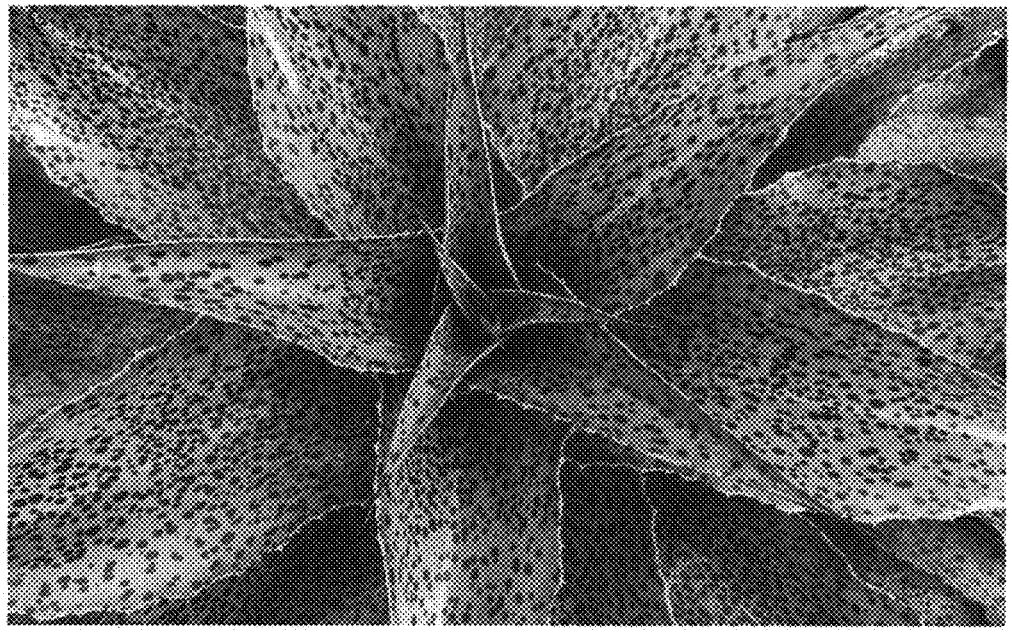
FIG. 2 shows a close-up of the foliage with dense spots and marginal leave spines of a plant grown outside for the third year.

The following descriptions and color references are based on the 2015 edition of The Royal Horticultural Society Colour Chart except where common dictionary terms are used. The new plant, X *Mangave* 'Spotty Dotty', has not been observed under all possible environments. The phenotype may vary slightly with different environmental conditions, such as temperature, light, fertility, moisture and maturity levels, but without any change in the genotype. The following observations and size descriptions are of a three-year-old plant grown for the last year in the ground in Zeeland, Mich. with supplemental water and fertilizer as needed.

Parentage: The female or seed parent is X *Mangave* H10-2 (not patented), a selected cross of *Manfreda maculosa* X *Agave gypsophylla*; the male or pollen parent is selection of *Agave bovicornuta* (not patented);

Propagation: Division of side shoots and sterile shoot-tip tissue culture;

Time to initiate roots from tissue culture: About 21 days;

Growth rate: Moderate to rapid;

Crop time: About 12 to 14 weeks to finish in a 3.8 liter container from a 35 mm tissue culture growing at about 21° C.;

Rooting habit: Fleshy, lightly branching, with roots up to 15 cm long;

Root color: Nearest RHS NN155A when active;

Plant shape and habit: Succulent herbaceous perennial with basal rosettes of about 50 to 60 leaves radially emerging and slightly arching from central rhizome, with lower leaves extending below the soil line when grown in containers, producing a radially-symmetrical, rounded mound;

Plant size: Foliage height about 28.0 cm tall from soil line to the top of the leaves and about 91.5 cm wide at the widest point below soil line in container;

Foliage description: Lanceolate; simple; margins coarsely bidentate; apex narrowly acute with flexible spine; base truncate, sessile, clasping; slightly concaved younger leaves, older lower leaves nearly flat; bi-laterally symmetrical; densely covered with small reddish-purple spots between 0.5 mm and 5.0 mm diameter, average about 3.0 mm diameter; glaucous both surfaces becoming lustrous adaxial;

Leaf size: To about 43.0 cm long, about 9.0 cm wide at base and about 4.0 mm thick at midrib; average about 37.0 cm long, about 7.0 cm wide and about 4.0 mm thick;

Marginal spines: Narrowly acute; two sizes, major spines about 2.0 mm long separated by one to three smaller spines of about 1.0 mm long; about eleven major spines per 10.0 cm;

Foliage fragrance: None observed;

Leaf blade color:

*Adaxial* (*young*).—Blend of between RHS 137D and RHS 143C with spots of nearest RHS N186C; Abaxial (young): blend between RHS 138B and RHS N138D with spots about nearest RHS N187A.

*Adaxial* (*mature*).—Nearest RHS 137B with spots between RHS N187A and RHS N186C.

*Abaxial* (*mature*).—Nearest RHS 138B and with spots between RHS N187A and RHS N186C.

*Marginal spines*.—Color (young) nearest RHS 160B; (mature) nearest RHS 175A.

Apical spine: Becoming dry and semi-flexible, entire; about 18.0 mm long and 2.0 mm across at base; color on young leaves nearest RHS 172A, at maturity nearest RHS 187A;

Petiole: Sessile;

*Veins*.—Parallel; not distinct abaxial or adaxial except mature adaxial midrib color between RHS 144A and RHS 144B.

Flower description: Not yet observed;

Fruit and seed: Not yet observed;

Disease resistance: X *Mangave* 'Spotty Dotty' has not been observed to be resistant to diseases beyond that which is normal for X *Mangave, Agave* or *Manfreda*. The plant is xeromorphic and survives well with minimal water once established. The new plant is hardy at least from USDA zone 9a to 11. Full extent of winter hardiness has not been tested.

It is claimed:

1. A new and distinct cultivar of ornamental X *Mangave* plant named 'Spotty Dotty' as herein described and illustrated.

* * * * *